United States Patent
Goodheart

(10) Patent No.: US 8,377,468 B2
(45) Date of Patent: Feb. 19, 2013

(54) DRY WOUND DRESSING AND DRUG DELIVERY SYSTEM

(75) Inventor: Clyde R. Goodheart, Lincolnshire, IL (US)

(73) Assignee: Rexaderm, Inc., Fort Lauderdale, FL (US)

( * ) Notice: Subject to any disclaimer, the term of this patent is extended or adjusted under 35 U.S.C. 154(b) by 530 days.

(21) Appl. No.: 12/439,197

(22) PCT Filed: Aug. 28, 2007

(86) PCT No.: PCT/US2007/077014
§ 371 (c)(1),
(2), (4) Date: Jun. 4, 2009

(87) PCT Pub. No.: WO2008/027904
PCT Pub. Date: Mar. 6, 2008

(65) Prior Publication Data
US 2009/0325861 A1   Dec. 31, 2009

Related U.S. Application Data

(60) Provisional application No. 60/840,265, filed on Aug. 28, 2006.

(51) Int. Cl.
*A61F 13/00* (2006.01)
*A61K 9/70* (2006.01)
*A61L 15/00* (2006.01)
*A61L 15/16* (2006.01)

(52) U.S. Cl. .......... 424/445; 424/443; 424/447

(58) Field of Classification Search .......... 424/443, 424/445, 447
See application file for complete search history.

(56) References Cited

U.S. PATENT DOCUMENTS

| | | | | |
|---|---|---|---|---|
| 2,693,438 | A | * | 11/1954 | Ward .......... 424/445 |
| 5,124,155 | A | | 6/1992 | Reich |
| 5,503,848 | A | | 4/1996 | Perbellini |
| 5,804,213 | A | * | 9/1998 | Rolf .......... 424/445 |
| 6,458,380 | B1 | | 10/2002 | Leaderman |
| 6,635,272 | B2 | * | 10/2003 | Leaderman .......... 424/443 |
| 6,828,308 | B2 | | 12/2004 | Mastradonato et al. |
| 2002/0122771 | A1 | * | 9/2002 | Holland et al. .......... 424/43 |
| 2002/0173485 | A1 | | 11/2002 | Mastradonato et al. |
| 2004/0029843 | A1 | | 2/2004 | Lawter |
| 2004/0254143 | A1 | * | 12/2004 | Mastradonato et al. .......... 514/54 |

FOREIGN PATENT DOCUMENTS

| | | |
|---|---|---|
| EP | 0526865 | 2/1993 |
| WO | 01/13967 | 3/2001 |
| WO | 02/09637 | 2/2002 |

OTHER PUBLICATIONS

International Search Report issued in PCT/US07/77014 (2008).
Hita-Iglesias et al., "Evaluation of the clinical behaviour of a polyvinylpyrrolidone and sodium hyalonurate gel (Gelclair<(>R)) in patients subjected to surgical treatment with CO2 laser," *Int'l Jrnl of Oral and Maxillofacial Surgery*, 35(6): 514-517 (2006).
Wright et al., "Chmotherapy-Induced Oral Mucositis: New Approaches to Prevention and Management," *Expert Opn on Drug Safety*, 4(2): 193-200 (2005).
Supplemental Search Report issued in application No. EP 07841486.9 (2010).
Search Report issued in European App. No. 12167927.8 (2012).

* cited by examiner

*Primary Examiner* — Fereydoun G Sajjadi
*Assistant Examiner* — Michael B Pallay
(74) *Attorney, Agent, or Firm* — Barnes & Thornburg LLP; Alice O. Martin

(57) ABSTRACT

Dry dressings incorporate drug-delivery systems for anti-infective agents, growth factors, fibronectin or other substances to enhance tissue healing. A pharmaceutical composition includes hyaluronate polyvinylpyrrolidone (PVP), maltodextrin, and hydroxyethylcellulose and glycerin in the form of a membranous, wafer-like material after being freeze-dried.

20 Claims, 2 Drawing Sheets

DRY WOUND DRESSING AND DRUG DELIVERY SYSTEM

CROSS-REFERENCE TO RELATED PATENT APPLICATIONS

This application is a U.S. Nationalization of International Patent Application no. PCT/US2007/077014, filed Aug. 28, 2007, which claims priority to U.S. Provisional Patent Application No. 60/840,265, filed Aug. 28, 2006, all of which applications are expressly incorporated herein by reference in their entireties.

Dry dressings incorporate drug-delivery systems for anti-infective agents, growth factors, fibronectin or other substances to enhance tissue healing.

BACKGROUND

Certain types of wounds are difficult to heal, e.g., diabetic leg and foot ulcers, venous stasis ulcers, decubitus ulcers, and severe burns. Dressings incorporating agents to assist healing such as fibronectins, or to control infection, such as antibiotics and antimicrobials, are an approach for use on difficult to heal wounds. However, storage of these "wet dressings" generally requires preservative agents, which are not optimal to place on wounds.

SUMMARY

A pharmaceutical composition includes hyaluronate, polyvinylpyrrolidone (PVP), maltodextrin, hydroxyethylcellulose, and glycerin in the form of a membranous, wafer-like material after being lyophilized (freeze-dried).

Other ingredients optionally include human cellular fibronectin (cFN), growth factors, antimicrobial agents, and a buffering system.

A dry wound dressing including the pharmaceutical composition is useful for treatment of abrasions, ulcers, burns, traumatic and surgical wounds.

The dressing may be in the form of an adhesive strip.

The dressing is useful to cover oral sores, mucositis or stomatitis resulting from chemotherapy, radiation therapy, dental braces, aphthous ulcers, or stem cell therapy, for chronic ulcers, such as diabetic ulcers, decubitus ulcers, and venous stasis ulcers.

Stomatitis, or other wounds that would benefit from the healing properties of fibronectin benefit from use of the dressing to deliver fibronectin. The incidence of post-operative adhesions is reduced.

A method to deliver agents such as fibronectin to a wound includes the steps of:
(a) obtaining a concentrated solution of an agent such as fibronectin;
(b) combining the agent with the dry wound dressing; and
(c) applying the dressing to the wound.

A suitable composition is made, before lyophilization, from about 0.04% to about 15% by weight/volume of hyaluronic acid, or a pharmaceutically acceptable salt thereof, having a molecular weight from about 500,000 daltons to about 2.2 million daltons; from about 1% to about 5% by weight/volume of a K60 to K100 polyvinylpyrrolidone.

Other ingredients optionally include an antibacterial agent, disinfectant agent, antifungal agent, antiviral agent, analgesic, anti-inflammatory, emollient, or a local anesthetic.

A composition used for treating or preventing inflammation in a patient includes administering to a patient in need thereof an effective amount of a composition made, before lyophilization, (i) from about 0.01 to about 5 percent by weight of hyaluronic acid, or a pharmaceutically acceptable salt thereof, having a molecular weight from about 500,000 to about 2.2 million daltons; (ii) from about 0.04% to about 15% by weight/volume of a K60 to K100 polyvinylpyrrolidone; and (iii) from about 86 to about 98% water.

A composition used for treating or preventing inflammation in the oral cavity of a patient includes administering to the oral cavity of a patient in need thereof an effective amount of a composition comprising, before lyophilization, (i) from about 0.01 to about 5 percent by weight of hyaluronic acid, or a pharmaceutically acceptable salt thereof, having a molecular weight from about 500,000 daltons to about 2.2 million daltons; (ii) from about 0.04 to about 15% by weight of a K60 to K100 polyvinylpyrrolidone;

A composition used for treating or preventing mucositis in a patient includes an effective amount of a composition comprising, before lyophilization, (i) from about 0.01 to about 5 percent by weight of hyaluronic acid, or a pharmaceutically acceptable salt thereof, having a molecular weight from about 500,000 daltons to about 2.2 million daltons; (ii) from about 0.04 to about 15% by weight of a K60 to K100 polyvinylpyrrolidone;

A composition used for treating pain resulting from oral surgery in a patient includes an effective amount of a composition comprising, before lyophilization, (i) from about 0.01 to about 5 percent by weight of hyaluronic acid, or a pharmaceutically acceptable salt thereof, having a molecular weight from about 500,000 daltons to about 2.2 million daltons; (ii) from about 0.04 to about 15% by weight of a K60 to K100 polyvinylpyrrolidone.

BRIEF DESCRIPTION OF THE DRAWINGS

FIG. 1 is the appearance of the lesion (about 12-15 mm) after the wound was treated with Bactroban for two weeks.

FIG. 2 was taken after two treatments of 48 hours each with the dry dressing.

FIG. 3 shows the cFN dressing applied to the wound.

FIG. 4 was taken after ten days of treatment, picture

FIG. 5 after two weeks, and picture

FIG. 6 after approximately one month.

Figure 1:
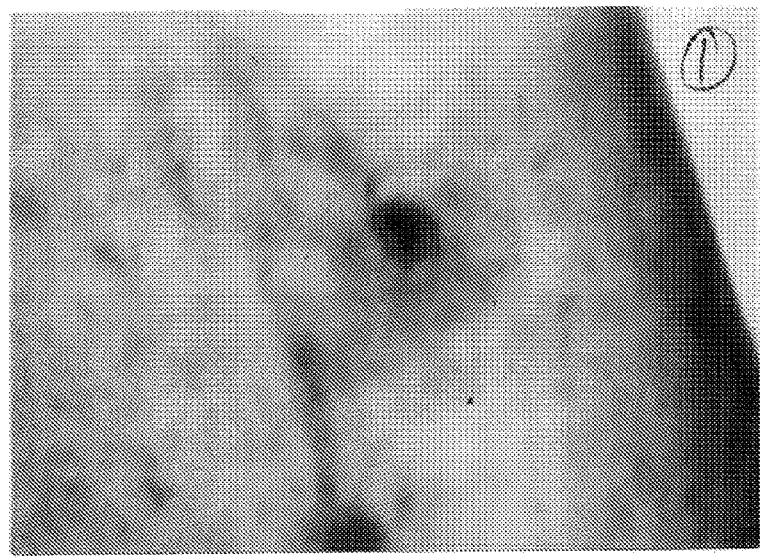
FIG. 1-6 are a series of 6 pictures taken sequentially after treatment of a leg ulcer, which had persisted for over 6 months without healing, using the dry dressing described herein that contained human cellular fibronectin (cFN).

The cFN dressing was held on with either a 4×4 sponge and tape or with a BAND-AID™ (adhesive bandage).

DETAILED DESCRIPTION

Pharmaceutical compositions described herein include the sodium salt of hyaluronic acid (also known as sodium hyaluronate or hyaluronan), polyvinylpyrrolidone (PVP), hydroxyethylcellulose, maltodextrin, glycerin and a buffering system, to which various other substances and medications may be added depending on the intended use of the composition. For example, for intraoral use, a suitable flavoring and sweetener may be added to enhance the taste. However, preservatives are not required, because the composition is lyophilized. The ingredients of the compositions have been approved by the U.S. Food and Drug Administration (FDA) for use in foods or in other pharmaceutical uses.

The pharmaceutical compositions provide dry wound dressings, drug delivery systems to administer medications or other substances to aid in wound healing, or to administer medications to limited areas of the body. The compositions, into which additional material is mixed before lyophilization to form a membrane or wafer-like material, may be prepared in a variety of thicknesses with a specific thickness appropriate for a given intended use. The thickness may be from less than a millimeter to a centimeter, with the preferred thickness for most purposes about 2 millimeters.

The formulation may also be made in specific configurations, by freezing it in a mold of the appropriate shape and size before lyophilization. For example, it can be made in the form of a plug to fit into a tooth socket following extraction, or into a curved piece in the shape of a fingernail or toenail, to be applied to a nail bed after avulsion of the nail. In another form, after lyophilization, the wafer-like material is easily ground into a powder, which powder can be sprinkled over the area to be treated, or it can be mixed with water or other liquid to reconstitute it into a paste-like material for application to the wound.

A carrier material for applying fibronectin to wounds was sought to make use of the well-known effectiveness of fibronectin in wound healing. Fibronectin is known to be unstable in solution, but it is stable for years in the lyophilized state, and it is difficult to incorporate it in a liquid or gel. Therefore, a dressing or carrier was sought that could contain fibronectin and that could be lyophilized. After testing a number of alternatives, it was found that the composition described herein accomplished the goal of providing such a carrier. Surprisingly, it was also found that the composition described could be used as a wound dressing and as a carrier or drug delivery system for a number of other pharmaceutical materials that are also involved in various ways in wound treatment.

A pharmaceutical composition is described that can be used without further ingredients ("basic"), or it may include one or more of the additional ingredients listed herein. The basic pharmaceutical composition is prepared by dissolving in purified water, all at room temperature with continuous mixing, the following: hyaluronic acid or a pharmaceutically acceptable salt thereof, preferably the sodium salt (also known as hyaluronan), with a molecular weight greater than 500,000 daltons, preferably of 2.2 million daltons or more (which can be obtained from Lifecore Biomedical, Inc., Chaska, Minn., among other suppliers) from 0.01% to 5.0% w/v; Maltodextrin (Aldrich Chemical catalog number 419672, dextrose equivalent 4.0-7.0) 0.5% to 5% w/v; PVP (polyvinylpyrrolidone) (Fluka Chemical catalog number 81440; molecular weight about 360,000 daltons, 0.04% to 15% w/v; and hydroxyethylcellulose (Spectrum Chemicals catalog number H1236; 5,000 cps) 0.1% to 3% w/v; and glycerin (reagent grade glycerin may be obtained from any of many general chemical supply companies). A pharmaceutical composition consists essentially of the following ingredients: 0.01 to about 5 percent by weight of hyaluronic acid, or a pharmaceutically acceptable salt thereof, having a molecular weight from about 500,000 to about 2.2 million daltons; (ii) from about 0.04 to about 15% by weight of a K60 to K100 polyvinylpyrrolidone.

In addition to the ingredients indicated, a buffer system is desirable for most purposes. For example, for the basic formulation to be used for mouth sores, a pH of about 7.4 (6.8 to 7.8) can be achieved with a phosphate buffer, preferably of 10 mM strength (5 mM to 50 mM), with 0.0312% w/v monosodium phosphate monohydrate and 0.2075% w/v disodium phosphate heptahydrate. Formulas for calculating phosphate buffers of other strengths and other pH values are readily available. A similar pH would be appropriate for matrix formulations to be used in the eye, in which tears have a pH of about 7.4 to 7.5. Other buffer systems, including organic buffers, may be used instead of the citrate and phosphate systems.

For matrix compositions to be applied to the skin, it is preferable to have the pH of the matrix approximately the same as that of the skin, which in humans is about pH 5.5. A citrate buffer, preferably of 10 mM strength (5 mM to 50 mM) can be used to obtain this pH, consisting of 0.0506% w/v anhydrous citric acid and 0.2233% w/v sodium citrate dihydrate. Formulas for calculating citrate buffers of other strengths and other pH values are readily available.

Other active pharmaceutical ingredients may be incorporated in the mixture as desired. Further, one or more of the ingredients listed may be omitted, to achieve various consistencies of the formulation for different intended purposes.

After thorough mixing, for example, the mixture is spread in a suitable flat-bottomed container to a depth of about 2 mm, and frozen. The depth of the mixture may be increased or decreased, if desired, to form a wafer of greater or lesser thickness, depending on the proposed use. Although a variety of containers may be used, polystrene is preferred, as it has been found that the matrix releases more readily from that surface than from other plastics or from glass. The containers of frozen mixture are then placed in a lyophilizer and dried directly from the frozen state. The resulting material after lyophilization is a light, fluffy, white membrane or wafer-like material, much like blotting paper. Depending on the proposed use, the membrane may be compressed by rolling to form a thinner, but tougher membrane.

When the composition is placed on a wound, it quickly absorbs moisture and adheres tightly to the surface, forming a protective covering. Although the dressing is adherent after it absorbs moisture, optionally it may be covered with tape or held in place with gauze or an elastic bandage. Antibiotics or other active pharmaceutical ingredients incorporated in the material are released into the wound. The pharmaceutical compositions or dressings may be sterile, e.g., by using filtered ingredients and by aseptic handling.

The following lists a number of possible applications of the composition. This list of 20 examples is for the purpose of exemplifying the myriad uses of the material, and is not meant to restrict the potential uses only to the examples in the list.

For oral lesions, including aphthous ulcers, ulcers resulting from dentures or from tooth braces, or ulcers or stomatitis resulting from chemotherapy, radiation, stem cell therapies, or other causes, the membrane or wafer is placed in the mouth and allowed to dissolve and coat the afflicted area. The formulation may also be used in a liquid form, by mixing the dried material (wafer-like or powder) with water, and used to treat pharyngitis, esophagitis, and gastritis, and can be administered rectally to treat proctitis, colitis, and similar conditions. The wafer-like membrane, in which soothing medications, including hydrocortisone, were incorporated, can be applied externally to hemorrhoids.

In the abdominal cavity, the compositions may be used post-operatively (e.g., bowel resection, explorations and the like) to decrease risk of adhesions, decrease risk of infections, improve surgical healing, and gain other therapeutic effects, such as its anti-inflammatory action.

Ophthalmic uses include treating conjunctivitis and keratitis, and post-operatively for any procedures involving the anterior and, possibly, posterior eye, either as firm or liquid dressings. For example, in the event of traumatic or viral keratitis, placement of a small piece of appropriately shaped membrane into the conjunctival sac allows drug delivery for 12 to 24 hours as well as adding "softness" to the natural lacrimation. This is also suitable for treating keratoconjunctivitis sicca (Sjogren's syndrome). Cellular fibronectin (cFN) may be incorporated in the material placed in the eye for treating nonhealing corneal ulcers.

In the genitourinary tract, the formulation may be used in the bladder or urethra, as a liquid dressing, or as a lavage solution.

Following avulsions of a fingernail or toenail, the wafer-like material can be used to maintain the integrity of the denuded nail bed. The biomaterial dressing is wetted about every 6 hours to provide a moist chamber for the nail bed and serve as drug delivery vehicle, for antibiotics or for cFN to protect the nail bed and assist in its healing.

For superficial skin wounds, including burns, abrasions, diabetic ulcers, venous stasis ulcers, decubitus ulcers, and traumatic or surgical wounds, the membrane or wafer-like material is placed over the area to be treated. The wounds may be those formed in the course of surgical procedures, including the wounds caused by removal of a nevus or skin cancer, the wounds resulting from Mohs surgical procedures, and wounds resulting from removal of skin for transplant. For this purpose, the wafer may have cFN and/or one or more growth factor(s), such as epidermal growth factor, incorporated in it. Moisture from the wound, in the form of blood or wound exudate, moistens the membrane or wafer-like material, causing it to adhere tightly to the wound. Saline or water can be used to moisten the area before placing the membrane if there is insufficient moisture from the wound. In another embodiment, the wafer may be made adherent to an adhesive strip, as in a Band-Aid™, which will hold it to the wound. In this way, the composition can deliver to the wound, agents to combat infection, and other substances to enhance healing, such as cFN.

The membrane or wafer-like material, to which cFN has been added, may be used to coat cut surfaces of tissues following surgery for cancers, such as breast cancer, to help decrease the incidence of local recurrence of the cancer, as described in Murthy et al. (1993), and in U.S. Pat. No. 5,354,269.

Various substances can be incorporated in the mixture before lyophilization to enhance the healing properties of the membrane; the specific medication or substance to be added depends on the use for that particular product. Alternatively, the membrane can be used without additional materials. Materials or medications to be incorporated in the membrane include, as examples, various antibiotics, anti-infectives, and antimicrobials, such as neomycin sulfate, penicillin, streptomycin; silver, sulfadiazine, or cerium nitrate; fibronectin; growth factors, such as epidermal growth factor, keratinocyte growth factor or fibroblast growth factor; topical anesthetic agents; hormones; chemotherapeutics, such as bleomycin or 5-fluorouracil (5-FU); or mixtures thereof. A list of potential applications of the compositions are in Table 1, which is intended only as examples, and it is not intended to limit the composition to those examples.

EXAMPLE 1

Preparation of Basic Dry Wound Dressing

A sample of the basic material was prepared as follows. Fifty mL of distilled water was placed in a 250 mL beaker equipped with a stir bar, on a magnetic stirring apparatus. Maltodextrin (Aldrich 419672; Lot 10910PD; Dextrose equivalent 4.0-7.0) 1.25, was added which dissolved quickly. Add PVP (polyvinlypyrrholidon) (Fluka 81440; Lot 1195730 51006177; MW ~360,000) 1.80 g, which required about 45 minutes to dissolve. Add hydroxyethylcellulose (Spectrum Chemicals H1236; Lot V00782; 5,000 cps) 0.30 g, which dissolved quickly, with stirring. Add sodium hyaluronate (Lifecore #81; Lot Dev 00453; MW 1.8 million) 0.05 g, which required several hours to dissolve, and the solution at this time was extremely viscous. Then 0.5 mL of reagent-grad glycerin was added. To buffer at pH 5.5, Sodium citrate, dihydrate (EM Chemicals, catalog number SX0445-1, lot 126351-113264) 0.1116 g and Citric acid, anhydrous (Sigma C-2404, Lot 080K1054) 0.0232 g were added. After all components were dissolved, the mixture was placed into flat-bottomed plastic vessels, which were placed in a freezer to harden, and were then lyophilized. The final product consisted of a dry, uniform, sponge-like wafer or matrix, which could be broken or cut easily. A summary of the preferred composition, and ranges of the various ingredients for different purposes of the composition, are set out in Table 2.

EXAMPLE 2

Dry Wound Dressing with Fibronectin

A 1 mg preparation of lyophilized human cellular fibronectin was reconstituted (U.S. Pat. No. 5,750,378) using 1.5 mL distilled water. Then 4.5 mL of the concentrated mixture described in Example 1 was mixed into the fibronectin solution. The whole was spread in the bottom of a flat-bottomed plastic container, frozen, and lyophilized along with the samples in Example 1. This preparation resembled the compositions without the fibronectin, except that it appeared to be less friable.

EXAMPLE 3

Dry Wound Dressings of Examples 1 and 2 on a Leg Wound

Figure 2:
Figure 3:
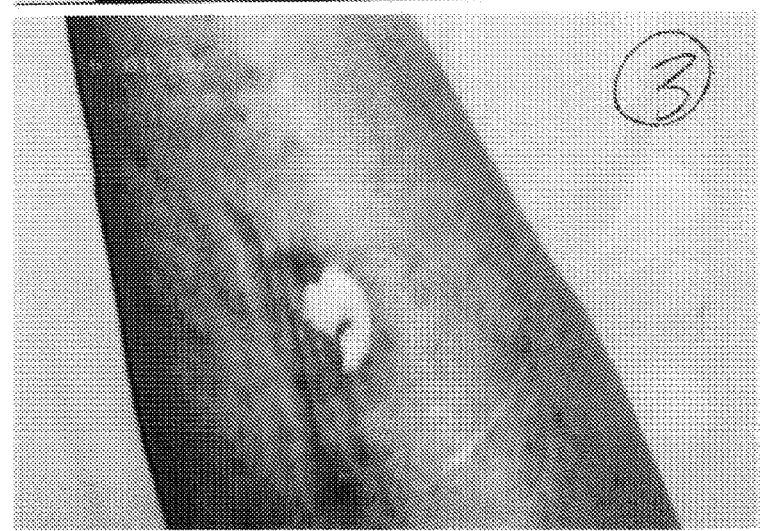
Figure 4:
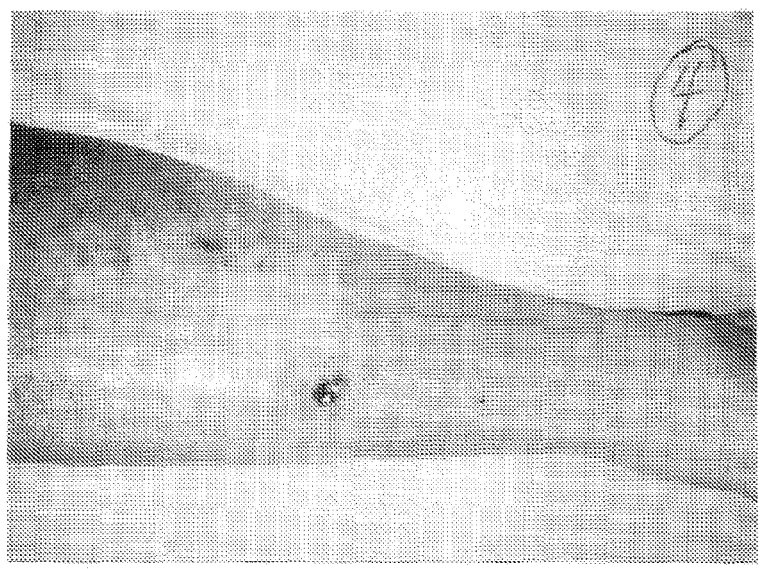
Figure 5:
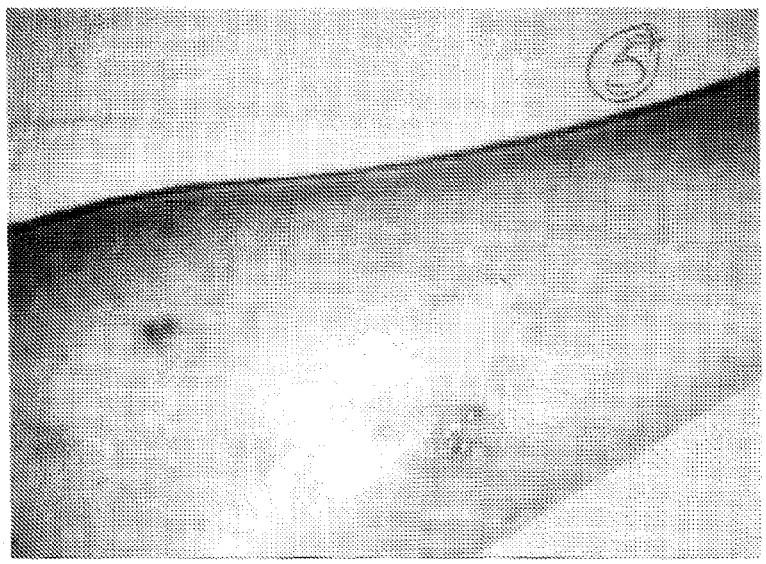
Figure 6:

This is a case report of a 72-year old white man who had a diabetic leg ulcer that had persisted about one year. A few months after the lesion occurred, a dermatologist obtained a biopsy sample, and the ulcer became infected, resulting in a larger lesion that was greatly inflamed. The lesion was treated with Avelox™. It appeared to heal in a few months, when the patient removed what appeared to be dead skin. The lesion opened again, and the patient treated it with Neosporin, Iodine, and Merthiolate. The dermatologist took a swab of the lesion. After the patient used the Bactro-Ban (Muciprocin) recommended by the dermatologist for two weeks, the wound became worse so the patient sealed it with Merthiolate. A bleeding lesion the size of a nickel persisted. The patient began treatment with cFN wound dressing of Example 2 about two weeks later, changing the dressing every 48 hours except for the first day. (The first change was at 24 hours). For the first 4 days, the material was fixed to the wound with a 4×4 gauze pad and an ACE bandage, then with a Band-Aid. After 6 days, the lesion that began as a serous, weeping, raw lesion the size of a nickel (15 mm) had gone down to the diameter of a pencil eraser (4 to 5 mm). After about 1 week of cFN treatment, only a small <2 mm spot remained. Treatment was discontinued for a few weeks, and then the lesion healed completely after another application of the matrix material containing cFN. Pictures of the lesion along the way at each change are shown in FIGS. 1-6.

EXAMPLE 4

Evaluation of Antimicrobial Activity

The in vitro antimicrobial activity of the composition was tested using the standard Kirby-Bauer method. Samples designated "Base" were the basic matrix material without added antimicrobials. The sample designated "Base+Silver" additionally contained silver sulfadiazine at pre-lyophilization concentration of 1% w/v. The sample designated "Base+Cerium" contained additionally cerium nitrate at a pre-lyophilization concentration of 0.4% w/v, and the sample designated "Base+Silver+Cerium" additionally contained both compounds at the above concentrations.

Results:

| MICROORGANISM | RESULT |
|---|---|
| SAMPLE 1: Dressing base | |
| *Salmonella choleraesuis* (ATCC 10708) | Not Satisfactory* |
| *Staphylococcus aureus* (ATCC 6538) | Not Satisfactory* |
| SAMPLE 2: Dressing - base + silver | |
| *Salmonella choleraesuis* (ATCC 10708) | Satisfactory** |
| *Staphylococcus aureus* (ATCC 6538) | Satisfactory** |
| SAMPLE 3: Dressing - base + cerium | |
| *Salmonella choleraesuis* (ATCC 10708) | Satisfactory** |
| *Staphylococcus aureus* (ATCC 6538) | Satisfactory** |
| SAMPLE 4: Dressing - base + silver + cerium | |
| *Salmonella choleraesuis* (ATCC 10708) | Satisfactory** |
| *Staphylococcus aureus* (ATCC 6538) | Satisfactory** |

*Not Satisfactory: Absence of formation of clear zone of inhibition in the agar around the sample, not indicating bacteriostatic activity.
**Satisfactory: Formation of a clear zone of inhibition in the agar around the sample, indicating bacteriostatic activity.
CONCLUSIONS: Analyzed samples were satisfactory as shown by the bacteriostatic activity over the microorganisms tested above, with exception of the sample 1 (base). The bacteriostatic activity was more pronounced on the sample 3 (base + cerium).

EXAMPLE 5

Evaluation of Skin Irritation

Samples of the matrix material containing cerium nitrate were tested for possible skin irritation at an independent contract laboratory in Brazil, using an appropriate, standardized protocol. The translation of their report follows:

EXAMPLE 6

Toxicity Studies

A. Primary Cutaneous Irritation in Rabbits (with Dressings Containing Cerium Nitrate)

These tests were performed according to ANVISA (Agência Nacional de Vigilância Sanitária, the Brazilian equivalent to the U.S. Food and Drug Administration) rules.

Animals: 6 rabbits (*Onyctolagus cuniculus*), 3 males and 3 females, young adults, not pregnant, weighting 2-5 Kg.

24 hours before the tests two 6 cm$^2$ areas were shaved, one in each flank, without skin lesions.

Each dressing was applied, covered with gauze and fixed with a hypoallergenic adhesive plaster (right flank).

After 4 hours the dressings were removed with purified water and the animals were examined after 24 and 72 hours. The areas were compared with control ones (left flank).

The grade of redness and edema was evaluated with a standardized scale from 0 to 4 and then the medium values were computed.

Following the results obtained the dressing was considered as "not irritant".

B. Acute Dermal Toxicity in Rats

These tests were performed according to the method of OECD (Organization for Economic Cooperation and Development) no 402, adopted in 1987, and ANVISA rules.

Animals: 10 Wistar rats: 5 males, 5 females, young adults, weighting 200-300 g.

24 hours before the procedure the animals were shaved.

The substance was applied over a piece of gauze and then on the animals' skin and fixed with a hypoallergenic adhesive plaster. The animals were observed for the following 14 days and data as morbidity, death and macroscopic pathological observation were registered.

There were no symptoms, reactions or death related to the substance applied. According to the results obtained the dressing with Cerium Nitrate presents dermal $DL_{50}$ over 2000 mg/Kg of weight.

C. Evaluation of the Repeated Cutaneous Irritation in Rabbits (with Dressings Containing Cerium Nitrate)

These tests were performed according to ANVISA rules.

Animals: 6 rabbits (*Onyctolagus cuniculus*), all males, adults, weighting 2-3 Kg. 24 hours before the tests two 6 cm$^2$ areas were shaved, on the animals' back without skin lesions.

Each dressing was applied, covered with gauze and fixed with a hypoallergenic adhesive plaster (right flank).

After 4 hours the dressings were removed with purified water. The dressing was applied daily for ten consecutive days. The animals were examined after 24 and 72 hours after the last dressing application. The areas were compared with control ones (left flank).

The grade of redness and edema was evaluated with a standardized scale from 0 to 4 and then the medium values were computed.

Considering the results found and the employed methods the repeated cutaneous irritation index of this dressing was zero, being classified as "not irritant product".

TABLE 1

| | Proposed Indication |
|---|---|
| Matrix: Actual additions | |
| Plain (no medications) | Mucositis, avulsion of the nails |
| Plain, but increased hyaluronan | To prevent adhesions in abdominal surgery |
| | Treat keratoconjunctivitis sicca |
| Cellular fibronectin (cFN) | Wound healing (clean wounds, Mohs surgery, eg) |
| | Corneal ulcers |
| | Inhibit local recurrence of cancer |
| Penicillin | Skin infection (impetigo, eg) |
| Streptomycin | Skin infection (impetigo, eg) |
| Silver sulfadiazine (Ag) | Skin infection (general, especially MRSA) |
| Cerium nitrate (Ce) | Burns, especially infected |
| Ag + Ce | Skin infection |
| Ag + cFN | Skin infection |
| Ce + cFN | Burns, with skin loss |
| Ag + Ce + cFN | Severely infected burns with skin loss (trauma, esp battlefield wounds) |

TABLE 1-continued

Proposed Indication

Have actually made a
"BandAid" with it as a pad
Matrix: Proposed additions

| | |
|---|---|
| Neomycin sulfate | Superficial skin wounds, with infection |
| Antivirals | Cold sores (herpes simplex, or genital herpes) |
| | Corneal ulcers due to viral infection; may also contain cFN |
| Hydrocortisone | Hemorrhoids, poison ivy |
| Antifungal agents | Athlete's foot, fungal nail infections, ringworm |
| Growth factors | Non-healing wounds |
| BMP ± VEGF | Non-union fractures, open reductions |
| | Coating for orthopedic and dental implants |
| Topical anesthetics | Painful wounds |

TABLE 2

COMPOSITION OF BASIC MATRIX

| INGREDIENT | Post-lyophilization Preferred % w/w | Pre-lyophilization Preferred Amount g or mL | Range Low | Range High |
|---|---|---|---|---|
| Purified Water | 0.00% | 100.0 | 100.00 | 100.00 |
| PVP (polyvinylpyrrholidone) | 46.15% | 3.6 | 2.50 | 4.50 |
| Maltodextrin | 32.05% | 2.5 | 1.60 | 3.80 |
| Glycerin | 12.82% | 1.0 | 0.50 | 3.00 |
| Hydroxyethylcellulose | 7.69% | 0.6 | 0.20 | 1.80 |
| Na Hyaluronate | 1.28% | 0.1 | 0.01 | 5.00 |
| | 100.00% | 7.8 | | |
| Examples of buffers, for 100 mL Citrate Buffer, 10 mM, pH 5.5 | | | | |
| Citric acid | | 0.0463 | | |
| Na Citrate | | 0.2233 | | |
| Phosphate Buffer, 10 mM, pH 7.4 | | | | |
| $Na(PO_4)_2 \cdot H_2O$ | | 0.0311 | | |
| $Na_2PO_4 \cdot 7H_2O$ | | 0.2075 | | |

Materials and Methods

Composition Formulation

The human cellular fibronectin (cFN) was prepared as described in U.S. Pat. No. 5,750,378. Human foreskin fibroblasts were obtained from Cambrex Bioscience (now part of Lonza Group, Ltd., Basel, Switzerland) and were grown to confluency in medium MCDB 105 (Sigma Chemical) supplemented with 5% fetal bovine serum; other fibroblast growth medium could also be used.

After expanding the cell population to result in confluent cells in several roller bottles (Tufrol, BD Falcon, Becton, Dickinson and Company, Franklin Lake, N.J.) the medium was changed to a production medium comprised of standard cell culture medium 199 (obtained as a dry powder from JRH Biosciences) prepared in tissue culture grade distilled water. The medium was supplemented with (g/L w/v) lactalbumin hydrolysate (Sigma Chemical, St. Louis, Mo.) 5 g; glucose (American Bioanalytical, Natick, Mass.) 3 g; HEPES buffer, sodium salt (American Bioanalytical) 1.735 g; HEPES buffer, acid (Sigma Chemical) 0.7943 g; dexamethasone (Sigma Chemical) 0.02 mg; penicillin G (Sigma Chemical) 100,000 units; streptomycin sulfate (Sigma Chemical) 0.1 g; sodium bicarbonate 2.2 g; insulin (Sigma Chemical) 10 mg. Note that no serum is added to the production medium.

The first addition of production medium was discarded from the roller bottles after two days, and was replaced with fresh production medium (100 mL/bottle). This conditioned medium was harvested every 3 to 4 days and replaced with fresh production medium. After harvesting, the conditioned medium was filtered through a fiberglass filter to remove any cells or cell debris, and was pumped through a gelatin-sepharose (GE Healthcare, Uppsala, Sweden) column. After rinsing the column bed with a dilute phosphate buffer to remove unattached proteins, the adherent fibronectin was eluted with CAPS buffer (Sigma Chemical) at pH 11.0 containing urea (American Bioanalytical) 4 mol/L. The peak fractions, determined by spectrophotometry at 280 nm, were pooled and further purified by passing through a Sephedex G-25 (Sigma Chemical) column to removed urea and salts, and to change the buffer to a dilute phosphate buffer. The peak fractions were pooled, and concentrated buffer added so that the final buffer would be physiologic after lyophilization. The solution was sterilized by passing through a sterile 0.22 μm filter, and was dispensed into sterile vials in a volume containing 1 mg of fibronectin per vial. The vials were frozen and lyophilized.

PUBLICATIONS

Murthy et al. (1993) [The role of fibronectin in tumor implantation at surgical sites. Clin. Exp. Metastasis 11(2):159-173.
U.S. Pat. No. 5,354,269

The invention claimed is:

1. A lyophilized pharmaceutical composition comprising hyaluronate, polyvinylpyrrolidone (PVP), maltodextrin, hydroxyethylcellulose, and glycerin in the form of a membranous, wafer material after being lyophilized.

2. The pharmaceutical composition of claim 1 further comprising one or more chemotherapeutic agents.

3. The pharmaceutical composition of claim 1 further comprising cFN.

4. The pharmaceutical composition of claim 1 further comprising growth factors.

5. The pharmaceutical composition of claim 1 further comprising an antimicrobial agent.

6. A dry wound dressing comprising the pharmaceutical composition of claim 1.

7. The dry wound dressing of claim 6 wherein the wounds are selected from the group consisting of abrasions, ulcers, burns, traumatic and surgical wounds.

8. The dry wound dressing of claim 6 in the form of an adhesive strip.

9. A method to cover wounds, the method comprising
    (a) selecting a wound, from the group consisting of oral sores, mucositis or stomatitis resulting from chemotherapy, radiation therapy, dental braces, aphthous ulcers, and stem cell therapy, and
    (b) applying the dry wound dressing of claim 6 to the wound.

10. The dry wound dressing of claim 7 wherein ulcers are selected from the group consisting of chronic ulcers, diabetic ulcers, decubitus ulcers, and venous stasis ulcers.

11. The pharmaceutical composition of claim 3 used to treat chronic ulcers, stomatitis, or other wounds that would benefit from the healing properties of fibronectin.

12. A method of decreasing the incidence of post-operative adhesions, the method comprising:
(a) obtaining the pharmaceutical composition of claim 1; and
(b) applying the pharmaceutical composition to the adhesion.

13. A method to deliver fibronectin to a wound, the method comprising:
(a) obtaining a concentrated solution of fibronectin;
(b) combining the fibronectin with the dry wound dressing of claim 6; and
(c) applying the dressing to the wound.

14. A lophilized composition comprising before lyophilization from about 0.01% to about 5% by weight/volume of hyaluronic acid, or a pharmaceutically acceptable salt thereof, having a molecular weight from about 500,000 daltons to about 2.2 million daltons; from about 0.04% to about 15% by weight/volume of a K60 to K100 polyvinylpyrrolidone, resulting in a membranous, wafer material lyophilization.

15. The composition of claim 14, further optionally comprising an agent that enhances tissue healing, the agent selected from the group consisting of an antibacterial agent, disinfectant agent, antifungal agent, analgesic, anti-inflammatory, emollient, a local anesthetic, and combinations thereof.

16. A lyophilized composition for treating inflammation in a patient comprising before lyophilization an effective amount of (i) from about 0.01 to about 5% by weight/volume of hyaluronic acid, or a pharmaceutically acceptable salt thereof, having a molecular weight from about 500,000 to about 2.2 million daltons; (ii) from about 0.04% to about 15% by weight/volume of a K60 to K100 polyvinylpyrrolidone; and (iii) from about 86 to about 98% water, resulting in a membranous, wafer material lyophilization.

17. The composition of claim 16 wherein the inflammation is in the oral cavity of the patient.

18. The composition of claim 16 wherein the patient has oral mucositis.

19. A lyophilized composition for treating mucositis in a patient comprising an effective amount of hyaluronic acid or a pharmaceutically acceptable salt thereof; and polyvinylpyrrolidone in the form of a membranous, wafer material.

20. The composition of claim 1 for treating pain resulting from oral surgery.

* * * * *

UNITED STATES PATENT AND TRADEMARK OFFICE
CERTIFICATE OF CORRECTION

| | |
|---|---|
| PATENT NO. | : 8,377,468 B2 |
| APPLICATION NO. | : 12/439197 |
| DATED | : February 19, 2013 |
| INVENTOR(S) | : Clyde R. Goodheart |

It is certified that error appears in the above-identified patent and that said Letters Patent is hereby corrected as shown below:

In the Claims

In Column 11, Claim 14, line 13, "lophilized" should be corrected to read --lyophilized--; line 19, the word --following-- should be inserted before the word "lyophilization".

In Column 12, Claim 16, line 12, the word --following-- should be inserted before the word "lyophilization".

Signed and Sealed this
Fourteenth Day of May, 2013

Teresa Stanek Rea
*Acting Director of the United States Patent and Trademark Office*